United States Patent [19]

Qasem

[11] Patent Number: 5,158,765

[45] Date of Patent: Oct. 27, 1992

[54] HAIR REMOVAL COMPOSITION

[75] Inventor: Patricia A. Qasem, 443 N. Newsome St., McKenzie, Tenn. 38201

[73] Assignees: Patricia A. Qasem; Abdullah Mohammad Qasem, McKenzie, Tenn.

[21] Appl. No.: 677,244

[22] Filed: Mar. 29, 1991

[51] Int. Cl.$^5$ ................................................. A61K 7/15
[52] U.S. Cl. ..................................... 424/73; 424/440; 424/465; 424/489; 424/61
[58] Field of Search .................. 424/465, 440, 489, 61, 424/73

[56] References Cited

U.S. PATENT DOCUMENTS

| | | | |
|---|---|---|---|
| 4,085,217 | 4/1978 | Kalopissis | 424/266 |
| 4,618,344 | 10/1986 | Wells | 8/161 |
| 4,832,949 | 5/1989 | Royal | 424/73 |
| 4,842,610 | 6/1989 | Gordon et al. | 424/73 X |

OTHER PUBLICATIONS

Remingtons Pharmaceutical Sciences, Mack Publishing Co. 1990.

*Primary Examiner*—Thurman K. Page
*Assistant Examiner*—Louis A. Piccone
*Attorney, Agent, or Firm*—Birch, Stewart, Kolasch & Birch

[57] ABSTRACT

A depilatory composition for the removal of hair is composed of a mixture of sugar, water and aspirin. This mixture is heated to dissolve the solute materials, and then allowed to cool so as to form a soft, pliable composition which can be manually applied to the skin. The composition firmly adheres to the hair with which it comes in contact, and by quickly drawing the applied material away from the skin, will cause the hair to be removed from its roots without causing undue irritation or swelling.

13 Claims, No Drawings

HAIR REMOVAL COMPOSITION

BACKGROUND OF THE INVENTION

1. Field of the Invention

This invention relates to hair removal compositions, and more particularly to a novel and improved hair removal composition with a soft consistency which is specifically adaptable for use in removing hair from the human body.

2. Description of Related Art

The removal of hair from the human body has received considerable attention. The hair and hair follicles can be removed by certain surgical operations or by electrolysis. It is also customary to remove hair by the use of tweezers or other instruments, but this does not have the same longlasting effects as surgical procedures. Moreover, the use of hair removal instruments is generally confined to removal of hair from a localized area, such as along the eyebrows or nostrils.

Creams or cold waxes have been formulated in the past for the purpose of hair removal to achieve more lasting effects, as well as to treat greater areas than are possible by pulling out individual hairs from localized parts of the body. For example, it has been proposed in the past to employ a combination of honey, rosin and wax which are heated together and thereafter combined with citric acid which is mixed into the composition until it has acquired a creamy texture, reference being made to U.S. Pat. No. 2,091,313 to W. M. Grant. Grant fails to state at what temperature the formulation is heated. Moreover, the use of a wax composition, such as beeswax, has been found to irritate the skin and cause redness and swelling.

British Letters Pat. No. 901,624 to E. Wenden discloses the formulation of a cream made up of sugar, lemon juice, glycerine, boric acid powder, sodium chloride, and a water carrier. These ingredients are heated to a temperature on the order of 278.F to form a plastic mass, and then allowed to cool to a temperature at which they may be poured into separate jars or containers. The resultant composition is applied to the skin so as to become matted with the hair, then immediately stripped from the skin to effect removal of the hair with the plastic mass.

Another British Letters Pat., No. 1,242,083 to M. Doughty, also discloses the combination of sugar with citric acid and water in the formation of a depilatory or hair removal composition. Generally, the approach taken in Doughty is to boil the mixture for a short period, or optionally, to simmer over longer periods, but makes no distinction as to the relative effect of boiling versus simmering. Once again, the resultant composition is alleged to be of a pasty consistency which will not harden when applied to the skin and, being water soluble, can be readily cleaned off the skin. Doughty proposes the optional addition of either a gelatin or isinglass. It has been found that the use of gelatin tends to leave a burning sensation when applied to the skin, as well as to cause swelling and discoloration. Moreover, the composition of sugar and gelatin as disclosed by Doughty would not appear to possess the capability of removing dead skin cells, or exfoliating the skin so as to leave a natural glow when the process is completed.

U.S. Pat. No. 4,832,949 to C. Royal discloses a depilatory composition made up of a mixture of honey, sugar, and citric acid. This mixture is heated, and allowed to cool, forming a highly viscous, wax-like composition which can be applied manually in slender strips to the skin. The composition firmly adheres to the hair with which it comes into contact, and causes the hair to be removed without undue irritation and swelling when quickly drawn away from the skin.

U.S. Pat. No. 4,842,610 to Gordon et al. discloses hair removal compositions comprising corn syrup and water. These compositions are used by applying them to the surface of the skin, pressing a sheet of paper or other fibrous material against the area, and subsequently lifting the sheet or peeling it off the skin surface to effect hair removal.

In the formulation of a depilatory composition, it is highly desirable that the composition can be readily applied with the fingers over a closely controlled area so as to uniformly and firmly adhere to the hair, and can be readily removed by grasping and pulling quickly away from the skin to effect the complete removal of hair over the applied area without the necessity of repeating the process. Further, in this connection, it is most desirable that the composition not cause swelling or other irritation to the skin.

SUMMARY OF THE INVENTION

It is therefore an object of the present invention to provide a novel and improved depilatory composition for the effective removal of hair from the skin.

Another object of the present invention is to provide a hair removal composition adaptable for use in removing hair from parts of the human body which can be quickly and easily formulated and produced, and which possesses good shelf life.

A further object of the present invention is to provide a novel and improved depilatory composition, and method of preparing the same, which can be applied to closely controlled areas of the human body for the purpose of complete and efficient hair removal from those areas without causing irritation or swelling, which is watersoluble, and which does not cause any substantial discoloration of the skin.

A still further object of the present invention is to provide a novel and improved depilatory composition which when applied to the skin is capable of removing dead skin cells, along with hair, which does not require repeated applications to the same area in order to effect complete removal of the hair down to the roots, and which is long lasting.

These objects and others are accomplished in accordance with the present invention by employing a novel and improved hair removal composition with a soft consistency which can be applied over selected areas of the skin to effect complete hair removal therefrom. In the preferred composition of the present invention, a major proportion of sugar is combined with a minor proportion of aspirin in water. The ingredients are stirred together over high heat, and the composition is heated for approximately 5.5 to 10 min., preferably 8 to 10 min., at a full boil (approximately 250.F). After the cooking operation, the composition is immediately removed from the heat and allowed to cool for approximately 25 min., whereupon it is ready for use, or for packaging in, for example, a tube dispenser. The resulting product remains soft after cooling, and does not discolor.

In applying the hair removal composition of the present invention to the skin, there is no need to heat it as it retains its soft consistency after cooling and during storage over extended time periods. The product is merely removed from its container and applied to the skin with one hand or one or more fingers of the hand. It is spread over and pressed onto the skin by hand in areas where hair is to be removed, and is worked into the hair so as to assure good adherence to the hair and skin over the desired area. Once applied in the above-described manner, the composition is allowed to remain on the skin for a brief period, and is then quickly pulled away from the skin with the fingers, using a jerking motion to effect complete hair removal.

The advantages of the present hair removal composition over other types of such products include the lack of any need to pre-heat or knead the composition before use; a very soft consistency which allows it to adhere well to the skin and remove minute hairs; lack of discoloration during storage and use; amenability to packaging in, for example, a tube-type dispenser; and reduction of irritation to the skin.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description

DETAILED DESCRIPTION OF THE INVENTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

DETAILED DESCRIPTION OF THE PREFERRED EMBODIMENT

In the preparation of the preferred composition of the present invention, one non-buffered 500 mg aspirin tablet or caplet was combined, in one-half cup of water, with one cup of sugar over high heat. Buffered aspirin can also be used. The sugar used was a fine granulated sugar, commonly referred to as sucrose. Other sugars may be employed, however. The ingredients were stirred thoroughly over high heat, and allowed to cook for 5.5 to 10 min. at a temperature on the order of about 250° F. Appropriate conversion must be made, in accordance with well known practice, in preparing the present composition at sea level or at other altitudes. Generally, the boiling point of any liquid is lower as the altitude increases, and the requisite cooking time is proportionally lengthened as the altitude increases.

The resultant mixture was found to be homogeneous when allowed to cool for about 25 min. At that point, the mixture could be transferred to a storage container or dispenser such as a tube dispenser, or used for hair removal. The product remains soft and pliable, and easy to work with. In that condition, the product when stored in individual closed containers has been found to have excellent shelf life, and can be stored for an indefinite period of time prior to use without discoloring. In accordance with well-known practice, the composition can also include additives such as germicides, preservatives, fragrances, aromatic substances, etc., and does not exhibit any tendency of the sugar to crystallize when stored over long periods of time.

For application purposes, a small quantity is placed on the index and middle fingertips of one hand, and then pressed into the skin in the area from which hair is to be removed. Extreme pressure is not required, although it may be desirable to go over the same area two to three times to assure uniform application and adherence of the composition over the area from which the hair is to be removed.

It is advisable to apply a limited quantity of the present composition to the desired area. Soon after application to the skin, i.e., within approximately 3 to 10 seconds, the material is quickly pulled off by hand much in the manner of removing a bandaid from the skin. The application procedure can then be repeated as described over or along adjacent areas where the hair is to be removed. Once the hair is removed, a wet, cold towel or washcloth may be applied to the area to close the pores and soothe the skin. Very little pain is experienced in the process of hair removal, with no resultant swelling or irritation beyond that which would be normally experienced in plucking individual hairs from the skin. Any redness or discoloration caused by removal of the hair was found to disappear within twenty-four hours.

The composition can be mixed and prepared in any desired quantities. Of particular importance is the heating procedure, to insure that the ingredients are heated to the proper temperature. At the inventor's altitude in McKenzie, Tenn., it was found that the optimum temperature for heating was 250.F., and the optimum cooking period was on the order of 8 to 10 min.

In the Examples which follow, the method of preparing the composition is exemplified. These Examples illustrate the quantity of ingredients and define the time period for cooking the same, but are not to be construed as limiting the present invention. As noted supra, modifications such as varying the exact nature and total amounts of starting materials, altitude, nature of the heating apparatus, etc. would be obvious to those skilled in the art, and are meant to be encompassed as equivalents by the present invention.

EXAMPLE I 1 cup of granulated table sugar (sucrose; approximately 7.25 oz.; 205.5 g by weight)
1 teaspoon of lemon juice
6–8 tablespoons of water The ingredients were mixed, and cooked on medium-high heat at approximately 225°–250° F. with constant stirring for 6 to 10 min. The mixture was then removed from the heat, and allowed to cool for 25 min. This composition turned brown within approximately 5 min., and required kneading until it became soft prior to use.

EXAMPLE II 1 cup of granulated table sugar (sucrose; approximately 7.25 oz.; 205.5 g by weight)
1 non-buffered aspirin tablet or caplet (acetylsalicylic acid; 500 mg; 0.5 g)
6 tablespoons of water The ingredients were mixed, and cooked at medium-high heat, 225°–250° F., until the aspirin and sugar were completely dissolved. The mixture was then removed from the heat, and allowed to cool for 25 min., at which time the composition was ready to use or to be poured into a squeeze tube dispenser.

EXAMPLE III 1 cup of granulated table sugar (sucrose; approximately 7.25 oz.; 205.5 g by weight)
1/2 cup of water (approximately 4 oz.; 113.4 g by weight)
1 non-buffered aspirin tablet or caplet (acetylsalicylic acid; 500 mg.; 0.5 g)

The aspirin was crushed and dissolved in the water on medium-high heat (225.F). The sugar was then added, and the mixture was stirred until reaching a full boil at 250° F. After cooking for min., the mixture was immediately removed from the heat, and allowed to cool for 25 min., at which time the composition was soft and ready to use. The composition could be stored at room temperature without discoloring.

EXAMPLE IV 1 cup of granulated table sugar (approximately 7.25 oz.; 205.5 g by weight)
1/2 cup of water (approximately 4 oz.; 113.4 g by weight)
1 non-buffered aspirin tablet or caplet (acetylsalicylic acid; 500 mg.; 0.5 g)

The same protocol as in Example III was followed, except that the mixture was cooked at 250° F. for 8-10 min. After removal from the heat and cooling, the composition was soft and ready to use. The composition could be stored at room temperature without discoloring.

The compositions of Examples III and IV were found to be easily applied to the skin, and possessed sufficient adherence such that they effectively removed the hair when lifted from the area of the skin to which applied.

In the working Examples given, the relative proportions by volume and weight as given are approximate, and may vary by ±one-half ounce.

The compositions of Examples III and IV comprise major proportions by weight of sugar and water, and a minor proportion by weight of aspirin; sugar is present in a greater proportion by weight than the combined proportions by weight of water and aspirin. In terms of the proportion of each individual component, sugar is present in the approximate ratio of 1.8 parts by weight for each part by weight of water, and approximately 411 parts by weight for each part by weight of aspirin.

On a relative basis, where sugar is present at 100 parts by weight, water is present at about 25 to 85 parts by weight based on the weight of sugar, more preferably at about 35 to about 75 parts by weight, and most preferably at about 45 to 65 parts by weight; aspirin is present at about 0.05 to 0.5 parts by weight based on the weight of sugar, more preferably at about 0.1 to about 0.4 parts by weight, and most preferably at about 0.2 to about 0.3 parts by weight.

Generally, in applying the composition to the skin for the purpose of removing hair, the skin should be dry, and free of oils and creams. The composition is spread on the skin by pressing down firmly, going over the same section two to three times if desired. The applied material is then pulled off quickly by lifting much in the manner or approach used to remove a bandaid.

After applying the composition over a desired area and removing as described, a cold wet towel or washcloth may be applied to the treated area to close the pores and soothe the skin, after which a skin lotion may be applied if desired.

The present formulation has demonstrated long-lasting effects in hair removal such that the process need not be repeated for weeks at a time.

The invention being thus described, it will be obvious that the same may be varied in many ways. Such variations, including those made in the specific composition and method of preparing and applying the same, are not to be regarded as a departure from the spirit and scope of the invention, and all such modifications as would be obvious to one skilled in the art are intended to be included within the scope of the following claims.

What is claimed:

1. A composition for the removal of hair from human skin, wherein said composition is to be applied to the human skin from which said hair is to be removed, comprising major proportions by weight of sugar and water, and a minor proportion by weight of aspirin, said sugar being present in a greater proportion by weight than the combined proportions by weight of said water and aspirin, said sugar, water, and aspirin being intermixed and heated to a temperature such that said aspirin imparts to said composition a soft, pliable consistency prior to application to the skin.

2. The composition according to claim 1, wherein said sugar is present in the approximate ratio of 1.8 parts by weight for each part by weight of water, and approximately 411 parts by weight for each part by weight of aspirin.

3. The composition according to claim 1, wherein said sugar is present at 100 parts by weight, said water is present at about 25 to about 85 parts by weight based on the weight of said sugar, and said aspirin is present at about 0.05 to about 0.5 parts by weight based on the weight of said sugar.

4. The composition according to claim 1, wherein said water is present at about 35 to about 75 parts by weight based on the weight of said sugar, and said aspirin is present at about 0.1 to about 0.4 parts by weight based on the weight of said sugar.

5. The composition according to claim 1, wherein said water is present at about 45 to about 65 parts by weight based on the weight of said sugar, and said aspirin is present at about 0.2 to about 0.3 parts by weight based on the weight of said sugar.

6. The composition according to claim 1, wherein said aspirin is buffered or unbuffered, and is derived from a tablet or caplet.

7. The composition according to claim 1, comprising:
   (a) 205.5 g of sugar;
   (b) 113.4 g of water; and
   (c) 0.5 g of aspirin.

8. A method for preparing a composition for the removal of hair from human skin and of applying said composition to skin from which said hair is to be removed, comprising the steps of:
   (a) intermixing major proportions by weight of sugar and water with a minor proportion by weight of aspirin, wherein the proportion by weight of said sugar is greater than the combined proportions by weight of said water and aspirin;
   (b) heating said sugar, water, and aspirin at an effective temperature for a time sufficient to dissolve said sugar and aspirin and produce a mixture thereof;
   (c) removing said mixture of step (b) from said heating and allowing said mixture to cool;

(d) applying said mixture of step (c) to the skin; and
(e) removing the applied mixture of step (d) from the skin after a brief period.

9. The method according to claim 8, wherein said sugar is present in a greater proportion by weight than the combined proportions by weight of said water and aspirin.

10. The method according to claim 8, wherein said sugar is present in the approximate ratio of 1.8 parts by weight for each part by weight of water, and approximately 411 parts by weight for each part by weight of aspirin.

11. The method according to claim 8, wherein said sugar is present at 100 parts by weight, said water is present at about 25 to about 85 parts by weight based on the weight of said sugar, and said aspirin is present at about 0.05 to 0.5 parts by weight based on the weight of said sugar.

12. The method according to claim 8, wherein said water is present at about 35 to about 75 parts by weight based on the weight of said sugar, and said aspirin is present at about 0.1 to about 0.4 parts by weight based on the weight of said sugar.

13. The method according to claim 8, wherein said water is present at about 45 to about 65 parts by weight based on the weight of said sugar, and said aspirin is present at about 0.2 to about 0.3 parts by weight based on the weight of said sugar.

* * * * *